United States Patent [19]

Steinman et al.

[11] 4,172,095

[45] Oct. 23, 1979

[54] NOVEL SYNTHESIS OF 3-AMINO-2-METHYLBENZOTRIFLUORIDE AND THE INTERMEDIATES THEREOF

[75] Inventors: Martin Steinman, Livingston; Yee S. Wong, Belleville, both of N.J.

[73] Assignee: Schering Corporation, Kenilworth, N.J.

[21] Appl. No.: 805,492

[22] Filed: Jun. 10, 1977

[51] Int. Cl.$^2$ .................. C07C 85/20; C07C 85/24; C07C 85/26

[52] U.S. Cl. .................................. 260/578; 260/582

[58] Field of Search ........................... 260/578, 609 R

[56] References Cited

U.S. PATENT DOCUMENTS 3,894,034   7/1975   Gassman et al. .................. 260/574 X

OTHER PUBLICATIONS

Claus, et al., "Tetrahedron Letters", No. 32, pp. 3607-3610 (1968).

Primary Examiner—Winston A. Douglas
Assistant Examiner—John Doll
Attorney, Agent, or Firm—Raymond A. McDonald

[57] ABSTRACT

This invention relates to a novel process for preparing 3-amino-2-methylbenzotrifluoride from 4-X-substituted-2-methylthiomethylbenzotrifluorides. The former compounds are useful in the preparation of anilino-nicotinic and anilino-anthranilic acids exhibiting analgesic, anti-inflammatory or anti-diarrheal properties. Some of the intermediates are novel per se.

9 Claims, No Drawings

NOVEL SYNTHESIS OF 3-AMINO-2-METHYLBENZOTRIFLUORIDE AND THE INTERMEDIATES THEREOF

FIELD OF THE INVENTION AND PRIOR ART

This invention relates to a novel synthesis of anilines. More particularly, this invention relates to a process whereby a 4-X-substituted-3-aminobenzotrifluoride is converted to 3-amino-2-methylbenzotrifluoride using inexpensive, readily available reagents and reaction conditions which are essentially non-hazardous. This invention also relates to novel 4-X-substituted-3-aminobenzotrifluoride intermediates.

In the prior art process (described in U.S. Pat. No. 3,390,172, issued June 25, 1968) for preparing 3-amino-2-methylbenzotrifluoride, 2-methyl-3-nitrobenzoic acid is treated with sulfur tetrafluoride at temperature in excess of 100° C. in a stainless steel bomb for about 15 hours under high pressure to produce 3-nitro-2-methylbenzotrifluoride. The nitro group is subsequently reduced by conventional means to yield the desired compound. The process presents a substantial hazard in that the high pressure could cause the reaction vessel to rupture, thereby releasing the corrosive reaction mixture. The probability of such a rupture is greatest when commercial scale batches are being produced. Further, sulfur tetrafluoride is of limited availability and is, therefore, an expensive reactant adding substantially to the cost of the overall process. We have now discovered a method for preparing 3-amino-2-methylbenzotrifluoride which obviates the use of high pressure. The process also obviates the use of scarce, expensive reactants thereby substantially reducing the cost and the hazard of producing the desired compound.

The prior art teaches that 3-amino-2-methylbenzotrifluoride is a valuable intermediate in the preparation of certain anilino-nicotinic and anilino-anthranilic acids, which compounds exhibit anti-inflammatory, anti-pyretic, anti-diarrheal, and/or anti-allergic activity. For example, U.S. Pat. No. 3,337,750, which issued Aug. 22, 1967, discloses that 2-(2-methyl-3-trifluoromethylanilino) nicotinic acid exhibits a number of the foregoing pharmacologic properties, and is, therefore, useful for treating such diseases as bursitis, gouty arthritis, spondylitis and the like. The process is also useful for preparing 2-(2-methyl-3-trifluoromethylanilino)-5-bromo-anthranilic acid, a compound which exhibits anti-diarrheal activity.

As previously stated, the process sought to be patented is one for preparing 3-amino-2-methylbenzotrifluoride which comprises: (a) condensing a 3-amino-4-X-benzotrifluoride with dimethylsulfoxide in the presence of an activating agent, (b) heating the N-(2-X-5-trifluoromethylphenyl)-S,S-dimethyl sulfimide at from about 85° to about 200° C. and (c) chemically reducing the so-formed 3-amino-4-X-2-methylthiomethylbenzotrifluoride, said X being hydrogen, chloro, bromo, iodo or alkylthio.

The foregoing process may be depicted as follows:

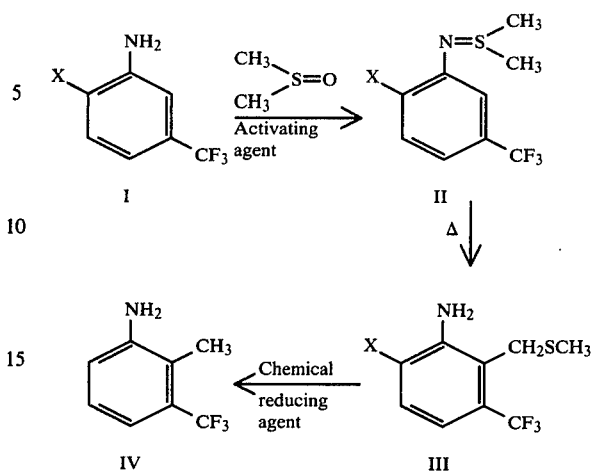

wherein X is a member selected from the group consisting of hydrogen, chloro, bromo, iodo and alkylthio.

The compounds sought to be patented are those compounds of formula III wherein X is a member of the group consisting of chloro, bromo, iodo and alkylthio, said alkyl group having 1 to 8 carbon atoms.

The condensation reaction may be effected at temperatures from ambient to about the reflux temperature of the reaction mixture, but is preferably effected at between 15° and 35° C. The reaction is usually permitted to proceed for from about 3 to about 12, preferably from about 6 to 8 hours in the presence of a tertiary amine acid acceptor such as triethylamine. The preferred solvents for the reaction are halogenated hydrocarbons, especially halogenated alkanes, such as methylene chloride, 1,2-dichloroethane, 1,3-dichloropropane and the like.

As used herein the term activating agent means those electrophiles which react with dimethylsulfoxide to produce reactive sulfonium salts. Exemplary of such agents are the acyl anhydrides, halogenated acyl anhydrides, dicyclohexylcarbodiimide, acyl halides, phosphorous pentoxide, polyphosphoric acid and the like. An excellent description of such agent is presented by Dawson et al. in the Journal of Organic Chemistry 42, 595 (1977).

The term alkylthio embraces R-S-groups wherein the sulfur atom is attached to the phenyl ring and R is alkyl having 1 to 8, preferably 1 to 3, carbon atoms.

The conversion of the compounds of formula II to those of formula III may be effected by heating the former from about 85° to about 200° C. The conversion may be effected in the absence of a solvent or in solvents such as halogenated hydrocarbons, aromatic hydrocarbons and cyclic ethers. Exemplary of such solvents are chloroform, 1,2-dichloroethane, benzene, toluene, xylene, dioxane, glyme, diglyme, triglyme and the like. The conversion is, preferably, effected in 1,2-dichloroethane in the presence of a tertiary amine such as, triethylamine. Alternatively, a sterically hindered alcohol may be used in lieu of the tertiary amine. The term sterically hindered alcohol embraces such alcohols as t-butanol 2-phenyl-2-propanol, 1,1-diphenylethanol, triphenylmethanol, 1-adamantanol and the like. These preferred conditions permit step A and step B to be effected as one continuous operation.

The term chemical reducing agent as used herein embraces such reducing agents or combination of agents as lithium aluminum hydride in combination with zinc chloride, Hopkins reagent (10% HgSO₄ in aqueous H₂SO₄), nickel boride, aluminum amalgum, Raney cobalt, lithium or sodium metal in ammonia, Raney nickel, especially W-2 Raney nickel. The reduction is preferably performed in water or water miscible organic solvents such as dimethyl formamide, tetrahydrofuran, dioxane, or alcohols including diols, such as ethylene glycol. The preferred solvents are water and lower molecular weight alcohols, such as methanol. The reaction is permitted to proceed for from about 1 to about 6 hours, i.e., until desulfurization is complete. The reaction may be effected at a temperature between ambient and the reflux temperature of the reaction mixture, preferably at about 60° to 75° C.

In those instances wherein the product of step (b) bears an X-substituent selected from the group consisting of chloro, bromo or iodo, the reductive desulfurization is preferably effected with W-2 Raney nickel in the presence of an alkali metal or alkaline earth metal hydroxide to facilitate the reductive dehalogenation which also occurs. Where X is a alkylthio substituent, the reduction medium need not contain an alkali.

In those instances wherein X is hydrogen, there is produced in addition to compound III, the 4-methylthiomethyl isomer thereof. Separation of compound III from its isomer is accomplished by fractional distillation.

The compound produced by this process, i.e. 3-amino-2-methylbenzotrifluoride is used in the preparation of anilino-nicotinic and anilino-anthranilic acid derivatives by methods generally known in the art such as by condensing the instant compound with a halogeno nicotinic or a halogeno anthranilic acid wherein said halogen occupies the 2-position on the acid moiety.

The following examples set forth the best mode known to us for practicing this invention. However, they should not be construed as limiting the scope thereof.

EXAMPLE 1

3-AMINO-2-METHYLBENZOTRIFLUORIDE

A. 3-Amino-2-methylthiomethylbenzotrifluoride

Add 426 g. of phosphorous pentoxide (3 moles) to 1.0 liter of 1,2-dichloroethane in a 5 liter, 3 necked round bottom flask equipped with reflux condensor, mechanical stirrer, thermometer and dropping funnel with a nitrogen inlet. Cool in an ice bath. Add 450 ml. of dimethyl sulfoxide (6 moles) dropwise to the well-stirred suspension. Maintain at 15°-25° C. with cooling. Add a solution of 322 g. of m-aminobenzotrifluoride (2 moles) in 708 g. of triethylamine dropwise over 2 hours keeping the temperature below 25° C. Stir for another hour, heat to 30° C. and maintain at 30°-35° C. for 4 hours. Cool in an ice bath. Add a mixture of 200 ml. t-butyl alcohol and 25 ml. of 1,2-dichloroethane, then heat to 85°-95° C. Keep at this temperature for about 16 hours. Cool the mixture to room temperature, pour onto a mixture of 120 g. of sodium hydroxide in water and 3 kg. of ice. Collect the organic layer. Extract the aqueous layer with a mixture of toluene and hexane and combine with the organic layer. Wash with 10% sodium hydroxide and then twice with water. Remove the organic solvent and distill at 2 mm, 75°-95° C. to yield the mixture of 3-amino-2-methylthiomethylbenzotrifluoride and 3-amino-4-methylthiomethylbenzotrifluoride. Separate the isomeric mixture by fractional distillation through a packed column in vacuo and obtain thereby 3-amino-2-methylthiomethylbenzotrifluoride boiling at 83° C. (2 mm) and 3-amino-4-methylthiomethylbenzotrifluoride boiling at 90° C. (2 mm).

B. 3-Amino-2-methylbenzotrifluoride

Wash 5 to 10 teaspoonsful of W-2 Raney nickel catalyst with distilled water to neutrality, then three times with absolute alcohol. Dissolve 10 g. of 3-amino-2-methylthiomethylbenzotrifluoride in 100 ml. of methanol and add 4 teaspoonsful of the W-2 Raney nickel. Reflux for 4 hours, filter to remove catalyst and evaporate solvent in vacuo to yield the title compound.

EXAMPLE 2

3-AMINO-2-METHYLBENZOTRIFLUORIDE

A.

3-Amino-4-chloro-2-methylthiomethylbenzotrifluoride

Add 106 g. of phosphorous pentoxide to 250 ml. of 1,2-dichloroethane in a 1 liter, 3 necked round bottom flask equipped with reflux condensor, mechanical stirrer, thermometer and dropping funnel with a nitrogen inlet. Cool in an ice bath. Add 112 ml. of dimethylsulfoxide dropwise to the well-stirred suspension. Maintain at 15°-25° C. with cooling. Add a solution of 98 g. of 3-amino-4-chlorobenzotrifluoride in 177 g. of triethylamine dropwise over 2 hours keeping the temperature below 25° C. Stir for another hour, then heat to 30° C. and maintain at 30-35° C. for 4 hours. Cool in an ice bath. Add a mixture of 50 ml. t-butyl alcohol and 6 ml. of 1,2-dichloroethane, then heat to 85°-95° C. Maintain at this temperature for about 16 hours. Cool the mixture to room temperature, pour onto a mixture of 30 g. of sodium hydroxide in water and 1 kg. of ice. Collect the organic layer. Extract the aqueous layer with a mixture of toluene and hexane and combine with the organic layer. Wash with 10% sodium hydroxide and then twice with water. Remove the organic solvent and distill through a packed column to obtain thereby the product of this step boiling 79°-85° C. (2 mm).

Alternatively, the 3-amino-4-chlorobenzotrifluoride may be replaced with equivalent quantities of 3-amino-4-bromobenzotrifluoride, 3-amino-4-iodobenzotrifluoride, 3-amino-4-methylthiobenzotrifluoride, 3-amino-4-ethylthiobenzotrifluoride, 3-amino-4-n-propylthiobenzotrifluoride, 3-amino-4-n-butylthiobenzotrifluoride, 3-amino-4-heptylthiobenzotrifluoride or 3-amino-4-octylthiobenzotrifluoride, and by following substantially the process of Example 2, step A, there is produced the following: 3-amino-4-bromo-2-methylthiomethylbenzotrifluoride, 3-amino-4-iodo-2-methylthiomethylbenzotrifluoride, 3-amino-4-methylthio-2-methylthiomethylbenzotrifluoride, 3-amino-4-ethylthio-2-methylthiomethylbenzotrifluoride, 3-amino-4-n-propyl-2-methylthiomethylbenzotrifluoride, 3-amino-4-n-butyl-2-methylthiomethylbenzotrifluoride, 3-amino-4-heptylthio-2-methylthiomethylbenzotrifluoride and 3-amino-4-octylthio-2-methylthiomethylbenzotrifluoride.

B. 3-Amino-2-methylbenzotrifluoride

Dissolve 2 g. of 3-amino-4-chloro-2-methylthiomethylbenzotrifluoride in 50 ml. of 90% ethanol which is 1N in potassium hydroxide. Add 2 teaspoonsful of Raney nickel (W-2). Stir at 70° C. for 3 hours, cool and filter. Add 50 ml. of water and extract three times with hexane. Dry the combined organic extracts and evaporate to yield the title compound.

Similarly, the 3-amino-4-chloro-2-methylthiomethylbenzotrifluoride may be replaced with equivalent quantities of 3-amino-4-bromo-2-methylthiomethylbenzotrifluoride, 3-amino-4-iodo-2-methylthiomethylbenzotrifluoride, 3-amino-4-methylthio-2-methylthiomethylbenzotrifluoride, 3-amino-4-ethylthio-2-methylthiobenzotrifluoride, 3-amino-4-n-propylthio-2-methylthiomethylbenzotrifluoride, 3-amino-4-n-butylthio-2-methylthiomethylbenzotrifluoride, 3-amino-4-heptylthio-2-methylthiomethylbenzotrifluoride, or 3-amino-4-octylthio-2-methylthiomethylbenzotrifluoride, and by following substantially the process of Example 2, step B, there is produced 3-amino-2-methylbenzotrifluoride.

We claim:
1. A compound of the formula:

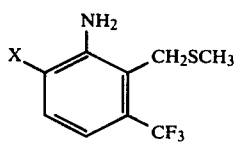

wherein X is a member selected from the group consisting of chloro, bromo, iodo and alkylthio, said alkyl group having 1 to 8 carbon atoms.

2. A compound of claim 1 wherein X is a halogen having an atomic weight greater than 19.

3. A compound of claim 1 wherein X is alkylthio, said alkyl group having 1 to 8 carbon atoms.

4. The compound of claim 2 wherein X is chloro, said compound being 3-amino-4-chloro-2-methylthiomethylbenzotrifluoride.

5. The compound of claim 2 wherein X is bromo, said compound being 3-amino-4-bromo-2-methylthiomethylbenzotrifluoride.

6. The compound of claim 2 wherein X is iodo, said compound being 3-amino-4-iodo-2-methylthiomethylbenzotrifluoride.

7. A compound of claim 3 wherein X is methylthio, said compound being 3-amino-4-methylthio-2-methylthiomethylbenzotrifluoride.

8. A compound of claim 3 wherein X is ethylthio, said compound being 3-amino-4-ethylthio-2-methylthiomethylbenzotrifluoride.

9. A compound of claim 3 wherein X is n-propylthio, said compound being 3-amino-4-n-propylthio-2-methylthiomethylbenzotrifluoride.

* * * * *